United States Patent
Lall

[19]

[11] Patent Number: 5,826,575
[45] Date of Patent: Oct. 27, 1998

[54] EXHALATION CONDENSATE COLLECTION SYSTEM FOR A PATIENT VENTILATOR

[75] Inventor: Suresh Lall, Escondido, Calif.

[73] Assignee: Nellcor Puritan Bennett, Incorporated, Pleasanton, Calif.

[21] Appl. No.: 816,719

[22] Filed: Mar. 13, 1997

[51] Int. Cl.⁶ ................................................. A61M 16/00
[52] U.S. Cl. .............................. 128/205.12; 128/205.27; 128/203.12
[58] Field of Search .................. 128/205.12, 204.21, 128/719, 203.12, 206.21, 205.27

[56] References Cited

U.S. PATENT DOCUMENTS

| | | | |
|---|---|---|---|
| 72,234 | 12/1867 | Sine | 128/207.16 |
| 3,454,005 | 7/1969 | Eubanks et al. | 128/205.12 |
| 3,991,762 | 11/1976 | Radford | 128/207.16 |
| 4,224,939 | 9/1980 | Lang | 128/207.14 |
| 4,327,718 | 5/1982 | Cronenberg | 128/205.12 |
| 4,457,305 | 7/1984 | Shanks et al. | 128/205.12 |
| 4,668,257 | 5/1987 | van der Meer et al. | 128/205.12 |
| 5,168,868 | 12/1992 | Hicks | 128/205.12 |
| 5,368,021 | 11/1994 | Beard et al. | 128/205.12 |
| 5,398,677 | 3/1995 | Smith | 128/205.12 |
| 5,524,615 | 6/1996 | Power | 128/205.12 |
| 5,558,087 | 9/1996 | Psaros et al. | 128/205.12 |
| 5,657,750 | 8/1997 | Colman et al. | 128/205.12 |

FOREIGN PATENT DOCUMENTS

| | | | |
|---|---|---|---|
| 18932 | of 1912 | United Kingdom | 128/205.12 |
| 1456570 | 11/1976 | United Kingdom | A62B 9/00 |

*Primary Examiner*—John G. Weiss
*Assistant Examiner*—V. Srivastava
*Attorney, Agent, or Firm*—Fulwider Patton Lee & Utecht, LLP

[57] ABSTRACT

The ventilator exhalation gas condensate collection and drainage system includes an exhalation filter and a fluid collector vial. Exhalation breathing gas flows through the collector vial for collection of condensate from the exhalation breathing gas. The exhalation filter includes a locking ring that can be turned to secure or release the fluid collector vial. A drain port on the collector vial can be connected to a drain tube, or can be capped by a drain port cap. A clamp on the tube can be unclamped to drain liquid from the collector vial. The collector vial includes a maximum fill line, to indicate when the collector vial should be emptied.

22 Claims, 3 Drawing Sheets

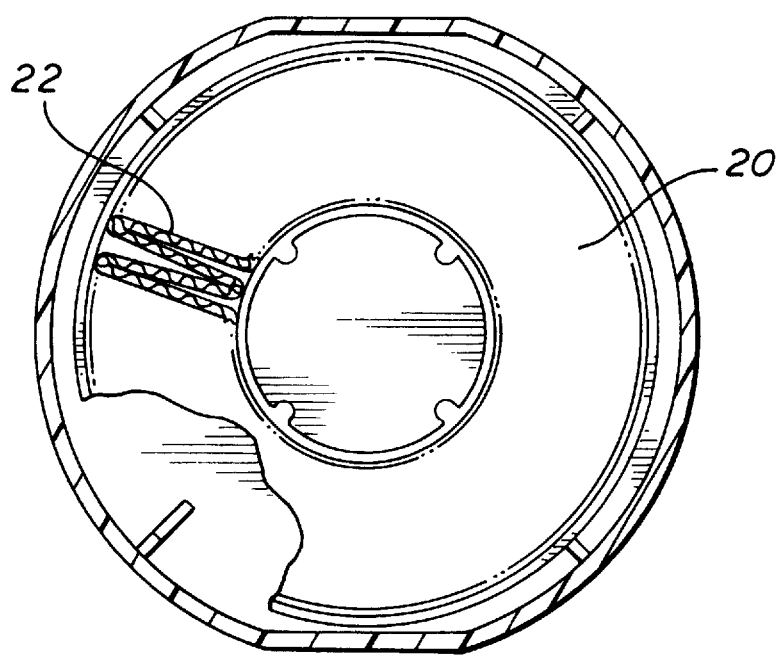
FIG. 5
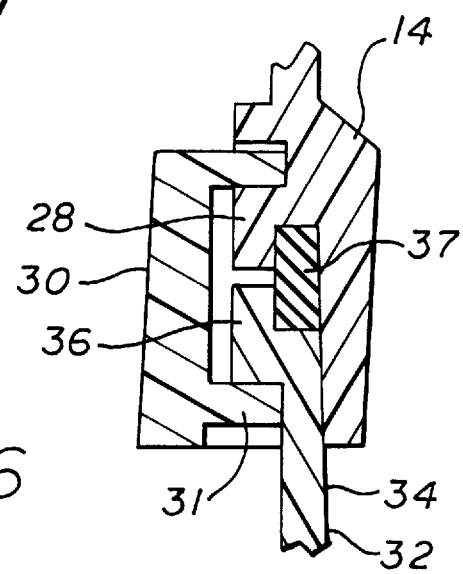
FIG. 6
FIG. 4
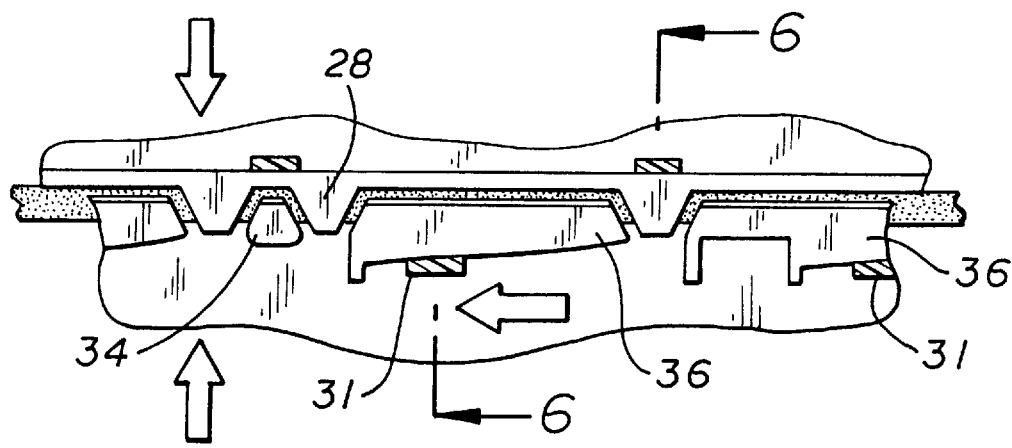

EXHALATION CONDENSATE COLLECTION SYSTEM FOR A PATIENT VENTILATOR

BACKGROUND OF THE INVENTION

1. Field of the Invention

This invention relates generally to breathing ventilators, and more particularly concerns a ventilator airway fluid collection system, including a fluid collector vial that is connected to an airway of the ventilator for controlling condensation through the exhalation circuit.

2. Description of Related Art

Modern patient ventilator systems conventionally provide a breathing gas to the patient airway at elevated pressure levels. Breathing gas is also often supplemented with a higher proportion of oxygen than is found in the ambient atmosphere, and is commonly humidified to prevent discomfort to the patient and drying out of the patients respiratory system. As the patient breathes, assisted by the ventilator, moisture in the exhaled breath is carried through the patient airway and out the exhalation path. Consequently, moisture regularly condenses in a ventilator airways, and one or more fluid collector vials can be placed in strategic locations in the airway to collect such fluid condensate.

A common problem with such fluid collection systems is that when such collector vials are removed to dispose of collected fluid, fluid can be sprayed out of the airway if the ventilator is operating when the fluid collection vial is removed, which can be unpleasant and unhygienic.

One known solution to this problem has been to provide spring loaded seals which close off the fluid collection opening in the airway when a collection vial is removed. However, such spring loaded seals can be expensive, difficult to clean, and can fail due to blockage of the seal, cracking of the seal, failure of the spring, and similar problems.

It is therefore desirable to provide a ventilator airway fluid collection system which is less complex and less expensive than prior art systems, is more robust and reliable than spring loaded seal systems, and that will allow collection and disposal of fluid from a ventilator, without requiring that the fluid collector vial be removed for emptying. It would also be desirable to provide such a ventilator airway fluid collection system that can readily be substituted for existing fluid collection systems. The present invention meets these needs.

SUMMARY OF THE INVENTION

Briefly, and in general terms, the present invention provides for a ventilator airway fluid collection system that permits the control of condensation in the exhalation circuit of a ventilator without the necessity of removing a fluid collector vial to dispose of fluid condensate.

Accordingly, the invention provides for a ventilator exhalation gas condensate collection and drainage system including a fluid collector vial with a drain port for removal of fluid condensate from the collector vial. The drain port can be capped by a drain port cap or plug, or can be connected to a drain tube. In a presently preferred embodiment, the collector vial includes a maximum fill line to indicate when the collector vial should be emptied. An exhalation filter can be provided that minimizes the particles and bacteria in the patient's exhaled gas, and protects the ventilator's exhalation and spirometry components.

In one presently preferred embodiment, the exhalation filter comprises a filter housing having a locking ring that can be turned to secure or release the fluid collector vial to the filter housing. The filter housing has a base with an opening to allow flow of exhalation breathing gas through the collector vial for collection of condensate from the exhalation breathing gas. The filter housing also contains a curved baffle deflector for the entry port which prevents direct flow of the exhalant towards the filter, thus avoiding unnecessary wetting of the filter and direct deposit of fluid into the collector vial.

In one currently preferred embodiment, an optional drain bag can be connected to the drain port of the collector vial via the drain tube. A clamp is typically installed on the tube. When the collector vial is to be emptied, the clamp on the tube to the drain bag can be unclamped to drain liquid from the collector vial to a disposable bag, providing a safe way of disposing of condensate.

These and other aspects and advantages of the invention will become apparent from the following detailed description and the accompanying drawings, which illustrate by way of example the features of the invention.

BRIEF DESCRIPTION OF THE DRAWINGS

FIG. 4 is an elevational partial sectional view of the interface of the locking ring, filter housing and collector vial of the exhalation condensate collection system of the invention taken along line 4—4 of FIG. 3;

FIG. 5 is a cross-sectional view of the exhalation filter of the exhalation condensate collection system of the invention taken along line 5—5 of FIG. 3; and FIG. 6 is an enlarged, fragmentary sectional view of the interface of the locking ring, filter housing and collector vial of the exhalation condensate collection system of the invention taken along line 6—6 of FIG. 4.

DETAILED DESCRIPTION OF THE PREFERRED EMBODIMENTS

Figure 1:
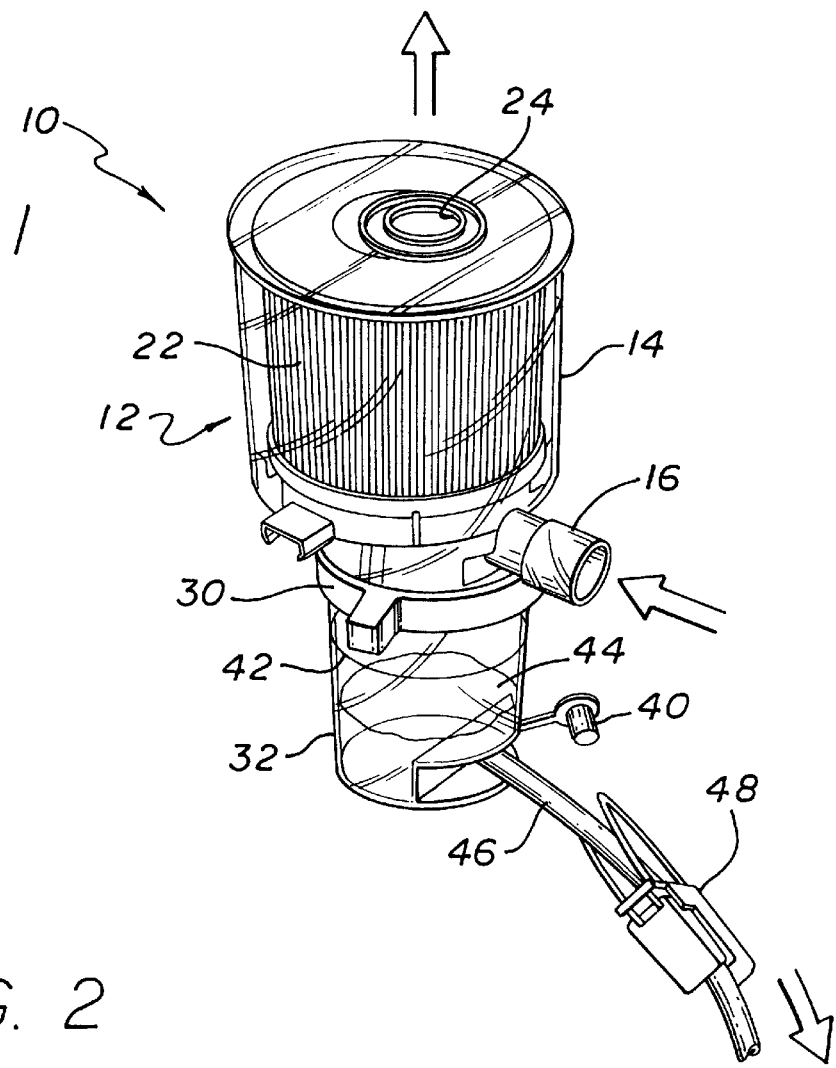
FIG. 1 is a perspective view of the exhalation condensate collection system of the invention.
Figure 2:
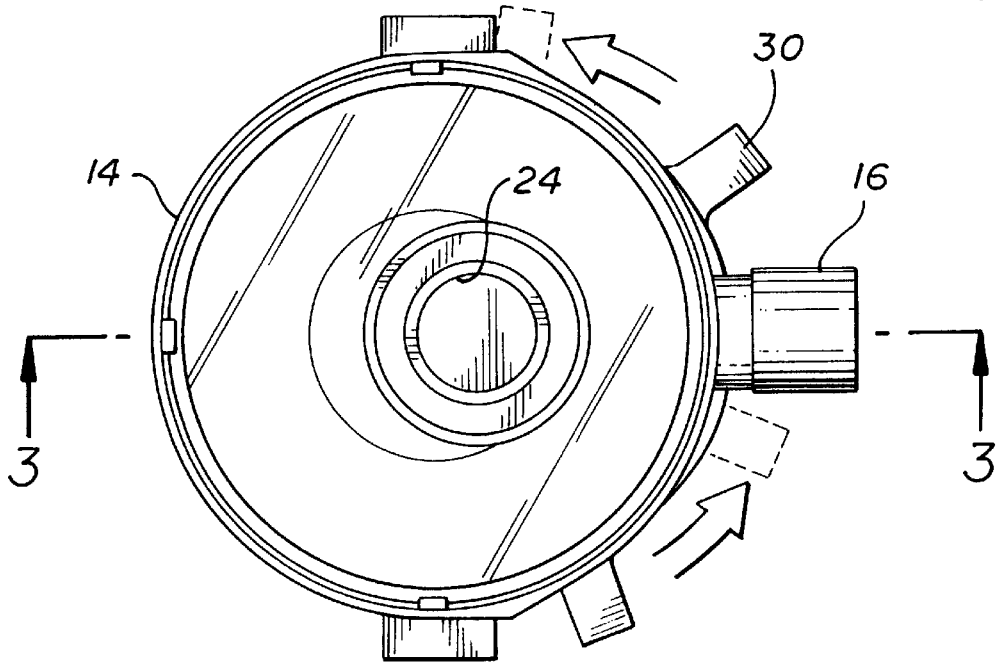
FIG. 2 is a top plan view of the exhalation filter and locking ring of the exhalation condensate collection system of FIG. 1.
Figure 3:
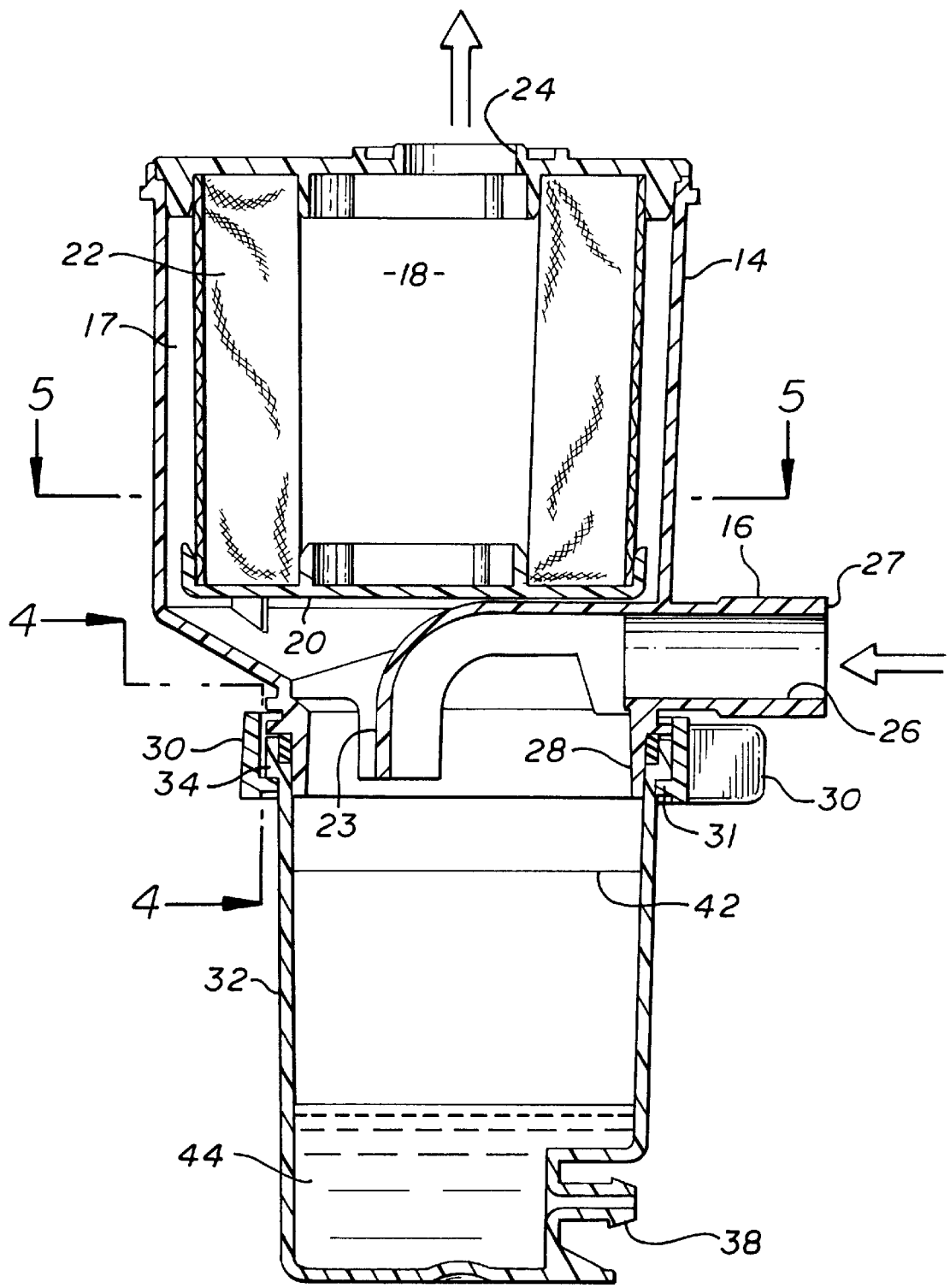
FIG. 3 is a cross-sectional view of the exhalation condensate collection system of the invention taken along line 3—3 of FIG. 2.

Fluid condensate from ventilator airways is typically collected by one or more fluid collector vials. However, fluid can be sprayed out of the airway if the ventilator is operating when a fluid collection vial is removed to dispose of collected fluid. Spring loaded seals to close off a fluid collection opening in the airway when a collection vial is removed can be expensive, difficult to clean, and can fail due to blockage of the seal, cracking of the seal, failure of the spring, and similar problems. Accordingly, the invention provides for an improved ventilator airway fluid collection system that allows collection and disposal of fluid from a ventilator without removal of the fluid collector vial.

As is illustrated in the drawings, in a currently preferred embodiment, the exhalation condensate collection system 10 for a patient ventilator includes an exhalation filter 12 having a filter housing 14 with an inlet connector 16, an exterior chamber portion 17, and an interior chamber 18. The exhalation filter minimizes the particles and bacteria in the patient's exhaled gas, and protects the ventilator's exhalation and spirometry components. The filter housing also has a filter support member 20 or base disposed within a lower portion of the interior chamber for supporting a filter element 22. The filter support member is spaced apart from the interior walls of the interior chamber of the filter housing, so that breathing gas can enter through the inlet connector 16, and flow through the fluid collector vial 32, the exterior chamber portion 17 and the filter element 22, into the interior chamber portion 18 and out the outlet 24 of the filter housing. A curved baffle deflector 23 continues internally from the inlet connector 16, curving toward the fluid collector vial 32 to deflect fluid condensate from the patient airway away from the filter and into the collector vial, with minimum resistance to air flow through the assembly of the filter and collector vial. The filters are reusable, and can be steam sterilized in an autoclave before the first use, and after each patient use. The filter element preferably has a particle filtration efficiency of a minimum of 99.97% of 0.3-$\mu$m nominal particle size at 100 L/min flow, and a viral and bacterial filtration efficiency of greater than 99.999%. The exhalation filter is also preferably designed to withstand repeated autoclave sterilization cycles at temperatures up to 135° C.(275° F.).

The filter housing inlet connector 16 for attaching the exhalation limb of the ventilator breathing circuit typically has an inner conical taper 26 that narrows slightly inwardly from the outside end 27, and an outer conical taper.

A locking mechanism is also provided for securing a collector vial to the filter housing, and for removing the collector vial from the filter housing, when necessary. The filter housing includes a plurality of bottom key flanges 28, extending below the inlet connector 16. A rotatable locking ring 30 is disposed on the bottom key flanges of the filter housing, and has tabs 31 generally extending perpendicularly from the locking ring for securing the fluid collector vial 32 to the filter housing. The collector vial has a top key flange 34 that interfits with a pair of adjacent bottom key flanges 28 of the filter housing, and a plurality of elongated locking flanges 36 having lower inclined sliding surfaces adapted to slidably interfit with the tabs 31 of the locking ring. A seal 37 is also provided between the bottom of the filter housing and the top of the collector vial to provide a tight assembly of the two.

The collector vial has a drain port 38 located at a lower portion of the collector vial for draining fluid from the collector vial. As is shown in FIG. 1, the drain port can be capped by a drain port cap or plug 40 attached to the drain port. In one currently preferred embodiment, the collector vial also includes a maximum fill line 42, to indicate when the collector vial is full of liquid 44 and should be emptied. The collector vial typically has a capacity (to the maximum fill line) of approximately 200 mL usable volume. The maximum fill line can be structurally molded in the collector vial, and is typically defined by a slightly raised shoulder or groove formed on the interior wall of the collector vial. The filter housing and collector vial can be molded from transparent plastic, such as polysulfone plastic, for example.

Referring to FIG. 1, an optional drain bag (not shown) can also be connected to the collector vial drain port by a drain tube 46, typically formed of flexible silicone or PVC tubing, for example. One end of the tube is secured to the collector vial drain port, and the other end of the tube is connected to the drain bag. The drain bag can have a connector (not shown) for connecting with the tubing. A reusable clamp 48 can be installed on the tube. When the collector vial is to be emptied, the clamp on the tube to the drain bag can be unclamped to drain liquid from the collector vial to the drain bag. Alternatively, the tubing can be connected to another type of fluid disposal container.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An exhalation condensate collection system for a patient ventilator having a ventilator airway for supplying breathing gas to a patient, comprising:

a collector vial adapted to be removably attached to the ventilator airway for receiving fluid condensate from breathing gas, said collector vial having a drain port for removal of fluid condensate from said collector vial; and an exhalation filter an inlet adapted to be connected to the ventilator airway for receiving breathing gas from the ventilator airway and in fluid communication with the collector vial, said exhalation filter including a filter housing, and a rotatable locking ring mounted to said filter housing for securing said fluid collector vial to the filter housing, said filter housing including a baffle in the inlet side of said filter housing to deflect the flow of exhaled gas away from said filter and into said collector vial.

2. The exhalation condensate collection system of claim 1, wherein the filter housing has a conical connector for attaching an exhalation limb of a ventilator breathing circuit.

3. The exhalation condensate collection system of claim 1, wherein said locking ring can be turned to lock or unlock the fluid collector vial in any position on the filter housing.

4. The exhalation condensate collection system of claim 1, wherein said collector vial further comprises a drain port cap for sealing said drain port.

5. The exhalation condensate collection system of claim 1, wherein said collector vial includes a maximum fill line to indicate when the collector vial should be emptied.

6. The exhalation condensate collection system of claim 1, wherein said collector vial further comprises a drain tube connected in fluid communication with said drain port for draining fluid condensate from said collector vial.

7. The exhalation condensate collection system of claim 6, further comprising a clamp disposed on said drain tube, whereby when said collector vial is to be emptied, said clamp on said drain tube can be unclamped to drain fluid condensate from the collector vial.

8. An exhalation condensate collection system for a patient ventilator having a ventilator airway for supplying breathing gas to a patient, comprising:

an exhalation filter having an inlet for receiving breathing gas from the ventilator airway and an outlet, said inlet including a baffle to direct breathing gas away from said filter into a collector vial, and an interior chamber for receiving breathing gas from the collector vial; and a collector vial removably attached to said exhalation filter for receiving breathing gas and fluid condensate from said ventilator airway and for collecting fluid condensate form breathing gas, said collector vial having a drain port for removal of fluid condensate from said collector vial.

9. The exhalation condensate collection system of claim 8, wherein said exhalation filter comprises a filter housing, and further comprising a rotatable locking ring mounted to said filter housing for securing said fluid collector vial to the filter housing.

10. The exhalation condensate collection system of claim 9, wherein the filter housing has a conical inlet connector adapted to be connected in fluid communication with the ventilator airway for attaching an exhalation limb of a ventilator breathing circuit.

11. The exhalation condensate collection system of claim 9, wherein said locking ring can be turned to lock or unlock the fluid collector vial in any position on the filter housing.

12. The exhalation condensate collection system of claim 8, wherein said collector vial further comprises a drain port cap for sealing said drain port.

13. The exhalation condensate collection system of claim 8, wherein said collector vial includes a maximum fill line to indicate when the collector vial should be emptied.

14. The exhalation condensate collection system of claim 8, wherein said collector vial further comprises a drain tube connected in fluid communication with said drain port for draining said fluid condensate from said collector vial.

15. The exhalation condensate collection system of claim 14, further comprising a clamp disposed on said drain tube, whereby when said collector vial is to be emptied, said clamp on said drain tube can be unclamped to drain fluid condensate from the collector vial.

16. The exhalation condensate collection system of claim 9, wherein said filter housing includes a plurality of bottom key flanges, and said rotatable locking ring is disposed on the bottom key flanges of the filter housing.

17. The exhalation condensate collection system of claim 16, wherein said collector vial has a top key flange, said filter housing includes a pair of adjacent bottom key flanges, and said top key flange interfits with said pair of adjacent bottom key flanges of the filter housing.

18. The exhalation condensate collection system of claim 9, wherein said locking ring has a plurality of tabs generally extending perpendicularly from the locking ring for securing the fluid collector vial to the filter housing.

19. The exhalation condensate collection system of claim 18, wherein said collector vial comprises a plurality of elongated locking flanges having lower inclined sliding surfaces adapted to slidably interfit with said plurality of tabs of said locking ring.

20. An exhalation condensate collection system for a patient ventilator having a ventilator airway for supplying breathing gas to a patient, comprising:

an exhalation filter having an inlet connected to the ventilator airway for receiving breathing gas from the ventilator airway and an outlet, said inlet including a baffle to direct said breathing gas away from said filter, said exhalation filter including a filter housing; and a fluid collector vial, a rotatable locking ring mounted to said filter housing for securing said fluid collector vial to the filter housing, said filter housing including a plurality of bottom key flanges, and said rotatable locking ring being disposed on the bottom key flanges of the filter housing, said collector vial being removably attached to said exhalation filter by said locking ring for receiving breathing gas and fluid condensate from the inlet of the filter and for collecting fluid condensate from breathing gas, said collector vial having a drain port for removal of fluid condensate from said collector vial.

21. An exhalation condensate collection system for a patient ventilator having a ventilator airway for supplying breathing gas to a patient, comprising:

an exhalation filter having an inlet connected to the ventilator airway for receiving breathing gas from the ventilator airway and an outlet, said inlet including a baffle to direct breathing gas away from the filter, said exhalation filter including a filter housing; and a collector vial having a top key flange, the filter housing including a pair of adjacent bottom key flanges, said top key flange intermitting with said pair of adjacent bottom key flanges of the filter housing, the filter housing having a rotatable locking ring mounted to said filter housing for securing the fluid collector vial to the filter housing, said rotatable locking ring being disposed on the bottom key flanges of said filter housing, said collector vial being removably attached to said exhalation filter by said locking ring for receiving breathing gas and fluid condensate from the inlet of said filter and for collecting fluid condensate from breathing gas, said collector vial having a drain port for removal of fluid condensate from the collector vial.

22. An exhalation condensate collection system for a patient ventilator having a ventilator airway for supplying breathing gas to a patient, comprising:

an exhalation filter having an inlet for receiving breathing gas from the ventilator airway and an outlet, said outlet including a baffle to direct said breathing gas away from said filter; and a collector vial removably attached to said exhalation filter for receiving breathing gas and fluid condensate from said ventilator airway and for collecting fluid condensate from breathing gas, said exhalation filter having a rotatable locking ring mounted to the filter housing for securing the fluid collector vial to the filter housing, said locking ring having a plurality of tabs generally extending perpendicularly from the locking ring for securing the fluid collector vial to the filter housing, and said collector vial having a drain port for removal of fluid condensate from said collector vial, wherein said collector vial comprises a plurality of elongated locking flanges having lower inclined sliding surfaces adapted to slidably interfit with said plurality of tabs of said locking ring.

* * * * *